US008715572B2

(12) United States Patent
Wu et al.

(10) Patent No.: US 8,715,572 B2
(45) Date of Patent: May 6, 2014

(54) METHOD AND APPARATUS FOR DETECTION, ANALYSIS, AND COLLECTION OF RARE CELLULAR EVENTS

(75) Inventors: Jiong Wu, Los Gatos, CA (US); Mahesh Junnarkar, Santa Clara, CA (US); Giacomo Vacca, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 21 days.

(21) Appl. No.: 13/473,495

(22) Filed: May 16, 2012

(65) Prior Publication Data

US 2012/0295339 A1 Nov. 22, 2012

Related U.S. Application Data

(60) Provisional application No. 61/488,066, filed on May 19, 2011.

(51) Int. Cl.
| | |
|---|---|
| *G01N 21/64* | (2006.01) |
| *G01N 15/06* | (2006.01) |
| *G06K 9/00* | (2006.01) |
| *G01N 15/02* | (2006.01) |
| *G01N 21/49* | (2006.01) |
| *G01N 21/85* | (2006.01) |
| *G01J 3/30* | (2006.01) |
| *G01N 21/00* | (2006.01) |

(52) U.S. Cl.
USPC .......... 422/73; 250/461.2; 250/373; 250/374; 250/375; 382/133; 356/317; 356/318; 356/337; 356/441; 356/442

(58) Field of Classification Search
None
See application file for complete search history.

(56) References Cited

U.S. PATENT DOCUMENTS 7,149,017 B2 * 12/2006 Kandori et al. ............ 359/202.1
7,804,594 B2    9/2010 Vacca et al.
(Continued)

OTHER PUBLICATIONS

G.Vacca et al., "Laser rastering flow cytometry: fast cell counting and identification", in Imaging, Manipulation, and Analysis of Biomolecules, Cells, and Tissues VII, Daniel L. Farkas; Dan V. Nicolau; Robert C. Leif, Editors, Proceedings of SPIE vol. 7182, Published Feb. 12, 2009.*

(Continued)

*Primary Examiner* — Jill Warden
*Assistant Examiner* — Julie Tavares
(74) *Attorney, Agent, or Firm* — Edward J. Baba; Benjamin C. Pelletier; Bozicevic, Field & Francis LLP

(57) ABSTRACT

Systems and methods for the detection, analysis, and collection of rare cellular events, wherein rare cellular events are defined by events comprising less than 5% of a total number of cells in a sample. The systems and methods generally include: (1) a flow cell dimensioned so as to permit a flow of a sample through the flow cell at a flow rate greater than 300,000 cells per second; (2) a laser positioned to emit a laser beam directed to the flow cell; (3) one or more deflector components disposed between the laser and the flow cell, wherein the deflector component is configured to affect a position of the laser beam relative to the sample flow; (4) one or more fluorescence emission detectors; and (5) one or more processor configured to detect rare cellular events based on fluorescence emission from cell-binding surface markers introduced into the sample prior to the sample being flowed through the flow cell.

22 Claims, 1 Drawing Sheet

(56) References Cited

U.S. PATENT DOCUMENTS

| | | |
|---|---|---|
| 7,943,342 B2 | 5/2011 | Tchistiakova et al. |
| 7,943,741 B2 | 5/2011 | Rosen et al. |
| 8,045,162 B2 | 10/2011 | Vacca et al. |
| 8,159,670 B2 | 4/2012 | Vacca et al. |
| 8,253,938 B2 | 8/2012 | Vacca et al. |
| 2002/0015971 A1* | 2/2002 | Verwer ................. 435/7.24 |
| 2009/0142765 A1* | 6/2009 | Vacca et al. ................. 435/6 |
| 2012/0270306 A1 | 10/2012 | Vacca et al. |

OTHER PUBLICATIONS

International Search Report for International Application No. PCT/US2012/038189, dated Sep. 21, 2012.

* cited by examiner

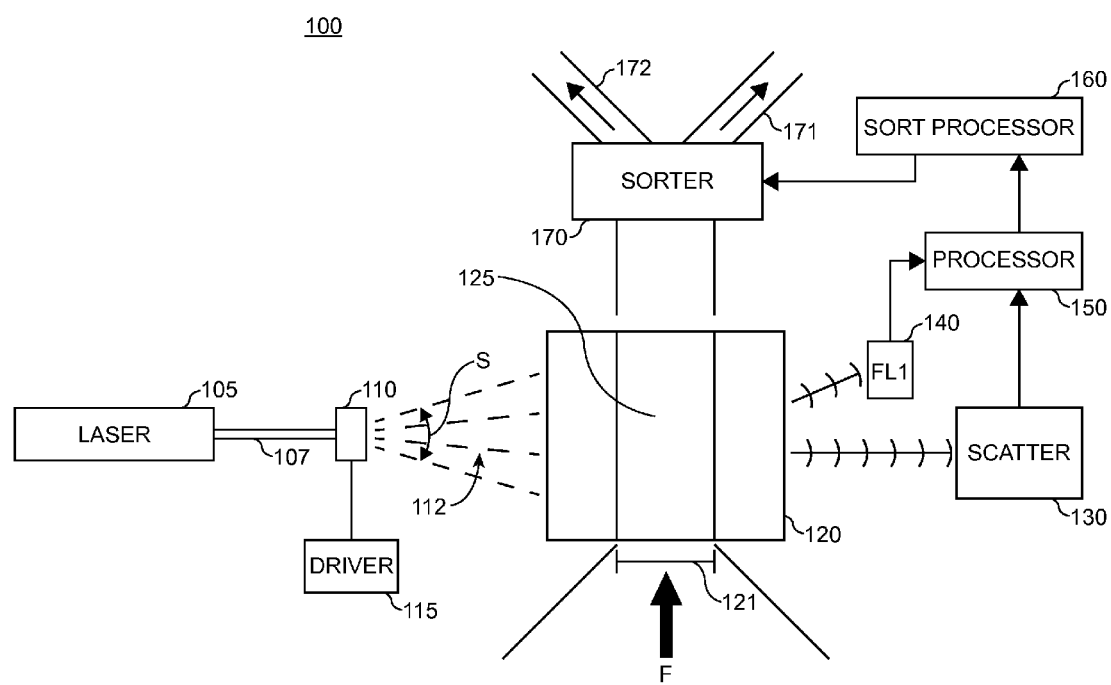

METHOD AND APPARATUS FOR DETECTION, ANALYSIS, AND COLLECTION OF RARE CELLULAR EVENTS

CROSS REFERENCE TO RELATED APPLICATIONS

This application claims the benefit under 35 U.S.C. §119(e) of U.S. Provisional Patent Application No. 61/488,066, titled, Method and Apparatus For Detection, Analysis, and Collection of Rare Cellular Events, and filed on May 19, 2011, the entire disclosure of which is incorporated by reference herein.

This application is related to co-pending U.S. application Ser. No. 13/116,594, filed May 26, 2011; which is a continuation of U.S. application Ser. No. 12/880,523, filed Sep. 13, 2010, which issued as U.S. Pat. No. 8,045,162; which is a divisional application of U.S. application Ser. No. 11/934,277, filed Nov. 2, 2007, which issued as U.S. Pat. No. 7,804,594; and which claims the benefit of U.S. Provisional Application No. 60/877,874, the disclosures of which are herein incorporated by reference in their entireties.

This application is also related to co-pending U.S. application Ser. No. 13/448,216, filed Apr. 16, 2012; which is a continuation of U.S. application Ser. No. 12/262,431, filed Oct. 31, 2008, which issued as U.S. Pat. No. 8,159,670; and which claims the benefit of U.S. Provisional Application No. 60/985,360, filed Nov. 5, 2007, the disclosures of which are herein incorporated by reference in their entireties.

BACKGROUND

This invention relates to flow cytometry systems and methods. More specifically, this invention relates to systems and methods for analyzing blood samples to identify, classify, and/or quantify rare cellular events.

Examples of rare cellular events include: Circulating Tumor Cells (CTCs), Circulating Stem Cells (CSCs), fetal cells in maternal blood, circulating liver or kidney cells, etc. CTCs and CSCs are currently being used in clinical settings to monitor disease progression, effectiveness of treatment, relapse, and remission. Fetal cells in maternal blood are sought to perform minimally invasive genetic clinical tests on the developing fetus, without incurring significant health risks for both the fetus and the mother (e.g., in amniocentesis). Such clinically relevant cell populations, however, when they are present in peripheral blood at all, can be in exceedingly low concentrations (e.g., measured in thousands, hundreds, or even single digits of cells per milliliter). Since the natural concentration of healthy cells in blood is in the millions per milliliter (white blood cells) to billions per milliliter (red blood cells), identification and counting of rare cells requires a sensitivity of as much as 1 in $10^9$, rare cellular events per normal cellular events.

Prior analysis systems typically involve a complex, multi-part sample preparation process, which, combined with the detection approach used, has yield issues (e.g., losses of the cells of interest). Further, even if red blood cells are lysed in a sample preparation step prior to analysis, identification and throughput times for the detection and analysis of rare cellular events is resource-consuming and inefficient. Prior systems, for example, typically take hours to deliver results.

The systems and methods presented herein provide a reliable, high-throughput, high-yield, low-cost, cellular analysis system for the identification, counting, classification, and optionally segregation of rare cellular events of interest.

BRIEF SUMMARY

Provided herein are systems and methods for analyzing blood samples, and more specifically for the detection, analysis, and collection of rare cellular events. Rare cellular events are generally defined as events comprising less than 5% of a total number of cells in a sample. The systems and methods generally include: (1) a flow cell dimensioned so as to permit a flow of a sample through the flow cell at a flow rate greater than 300,000 cells per second; (2) a laser positioned to emit a laser beam directed to the flow cell; (3) one or more deflector components disposed between the laser and the flow cell, wherein the deflector component is configured to affect a position of the laser beam relative to the sample flow; (4) one or more fluorescence emission detectors; and (5) one or more processors configured to detect rare cellular events based on fluorescence emission from cell-binding surface markers introduced into the sample prior to the sample being flowed through the flow cell.

BRIEF DESCRIPTION OF THE FIGURES

The accompanying drawing, which is incorporated herein, forms part of the specification. Together with this written description, the drawing further serves to explain the principles of, and to enable a person skilled in the relevant art(s), to make and use the systems and methods presented.

FIG. 1 is a schematic diagram of a flow cytometry analyzer, in accordance with one embodiment presented.

DESCRIPTION OF THE INVENTION

U.S. Pat. No. 7,804,594 ("the '594 patent"), which is incorporated by reference herein in its entirety, describes a method and apparatus for rapidly counting and identifying biological particles in a flow stream, using a laser rastering flow cytometer (LRFC). The systems and methods presented herein build on the systems and methods described in the '594 patent. For example, provided herein is a cellular analyzer, based on a LRFC, which is optimized for high-throughput of sample fluid through the flow cell. The detection channels (e.g., scattering, and fluorescence detection channels) are configured so as to discriminate rare target cells of interest (such as, e.g., Circulating Tumor Cells (CTCs), fetal cells in maternal blood, etc.) out of a large background population of "normal" blood cells (e.g., red blood cells (RBCs), white blood cells (WBCs), etc.). A combination of fluorescence and scattering signals may be used to identify the cells of interest. In one example, fluorescent dyes that bind to DNA are used as surface markers for the cells of interest. For example, fluorophore-conjugated monoclonal antibody assays may be used to label rare cells of interest. Labeling can be used to positively select the cells of interest, or for negative selection wherein cells specifically not-of-interest are identified and removed (e.g., using CD45 label to identify WBCs). An optional sorting module may be built into the system to allow for the segregation and capture of selected cells of interest for further analysis. Further analysis may include, for example, bright-field or fluorescence microscopy, Fluorescence In Situ Hybridization (FISH), etc.

The presented systems and methods address the above-described problems by using (a cocktail of) monoclonal antibodies to robustly distinguish target events (i.e., rare cellular events) from the non-target events (i.e., normal or healthy cellular events). Use of LRFC allows for the rapid scanning of raw analyte volume, thus making it practical to use a flow cytometric approach to detect rare events, which in turn affords a higher yield at a lower cost than is possible with alternate approaches.

FIG. 1 is a schematic diagram of a flow cytometry analyzer 100, in accordance with one embodiment presented. As would be appreciated by one of skill in the art, FIG. 1 is a schematic diagram depicting key system components for illustrative purposes only. Additional system units and sub-units, whether shown or not shown, are used to complete the functional aspects of a flow cytometry instrument. Such additional system units and sub-units are described in the literature, including the above-referenced patents and published applications, which have been incorporated by reference.

A laser 105 is provided, which emits a laser beam 107 in the direction of a flow cell 120. A deflector component 110 is positioned between the laser 105 and the flow cell 120 to sweep (S) the laser beam in vertical and horizontal directions 112 across an area of interrogation 125 within the flow cell 120. A driver 115, and corresponding processor (not shown), are used and configured to control the direction and speed of the deflector component 110. As such, the flow cytometry instrument is configured to function as a laser rastering instrument, as described in the above-reference patents and published applications.

In operation, a sample stream is flowed (F) through the area of interrogation (or interrogation zone) 125 of the flow cell 120. Typically, hydrodynamic focusing is used to create a sample core stream within a sheath fluid passing through an opening 121 of the flow cell 120. Flow rate control mechanisms (not shown) may be provided to control the speed and throughput of the flow (F) through the flow cell 120. When particles (e.g., cells; also referred to as "events") pass the area of interrogation 125, and are excited by the laser beam 107, light scatter and/or fluorescence emissions are detected by one or more optical detectors (such as scatter detector 130 and/or fluorescence detector (FL1) 140). Photomultiplier tubes (PMTs) and photodiodes are typically used for such optical detection. Optical scatter and fluorescence measurements are then submitted to a processor 150, wherein the signals are analyzed to identify the particles crossing the area of interrogation 125.

Commercial adoption of LRFC technology has been slow, however, due to the complexity in obtaining accurate measurements/analysis with increased throughput through the area of interrogation. Flow cytometry instruments, which mainly rely on detection of light scatter from particles of interest, are particular sensitive to the inaccuracies created by the increased coincidence (i.e., two or more particles passing the area of interrogation at the same time) caused by LRFC systems. As such, increasing the area of interrogation, flow rate, throughput, core stream size, laser beam spot size, and/or scanning speeds typically has a negative effect on the accuracy of measurements in an LRFC system.

The inventors of the present application, however, have determined that for the use-case of detecting rare cellular events (e.g., events fewer than 5% of the total number of events), the accuracy of measurement can be sacrificed in exchange for increased speed, throughput, and effective volume of detection. More specifically, the systems and methods presented herein incorporate the use of fluorescent surface markers, which attach to rare cell populations, and corresponding fluorescence measurements to obtain yes/no determinations on whether rare cells are present within a sample. If the system determines that such rare cells are present, such events can be sorted out of the sample, for a more detailed analysis (e.g., via microscopic examination). For example, if the processor 150 determines that rare cells have been identified, a signal is submitted to a sort processor 160 and associated sorter 170, to redirect particles of interest and particles not-of-interest into separate collection tubes 171 and 172.

TABLE 1 below shows a comparison between the operational parameters of traditional stationary cytometers, typical LRFC, and an LRFC configured in accordance with the present invention.

TABLE 1

| Parameter (control variable) | Traditional Stationary Cytometers | Typical Laser Rastering Cytometers | Presented Laser Rastering Cytometers |
| --- | --- | --- | --- |
| Laser beam spot size | 65 μm × 20 μm | 10 μm × 20 μm | >20 μm × 40 μm |
| Core stream size | 5 μm × 80 μm | 100 μm × 20 μm | >100 μm × 200 μm |
| Flow rate | 8 m/s | 6 m/s | >12 m/s |
| Throughput | 2.5 μL/s | 12 μL/s | >120 μL/s |
| Horizontal scanning speed | N/A | 100 m/s | >200 m/s |
| Vertical scanning speed | N/A | 5 m/s | >10 m/s |

As evident from TABLE 1 the flow cytometry instrument 100 is designed for significantly higher throughputs. Such increased throughputs would not be commercially feasible with modern processing technology, because such throughputs would result in a significant decrease of the accuracy of the analysis. However, as described above, for the use-case of detecting rare cellular events, such accuracy is sacrificed for increased speed, throughput, and effective volume of detection.

Further, because accuracy is no longer a concern, "low-grade" processors may be incorporated into the flow cytometry analyzer 100. As such, cheaper field programmable gate arrays, with lower signal processing capabilities, may be employed, while still meeting the objective of identifying clinically important rare cellular events. Additionally, milder lysis (or lysis-free single dilutions) and relatively shorter incubation times may be used to attach the appropriate surface markers on the cells of interest (when present), which prevents or minimizes the degradation of cell surface antigens.

Additional Embodiments

In one embodiment, there is provided a flow cytometry analyzer for the detection of rare cellular events. The analyzer comprises: (1) a flow cell dimensioned so as to permit a flow of a sample through the flow cell at a flow rate greater than 300,000 cells per second; (2) a laser positioned to emit a laser beam directed to the flow cell; (3) one or more deflector components disposed between the laser and the flow cell, wherein the deflector component is configured to affect a position of the laser beam relative to the sample flow; (4) one or more fluorescence emission detectors; (5) one or more light scatter detectors; and (6) one or more processors configured to detect rare cellular events based on fluorescence emission from cell-binding surface markers introduced into the sample prior to the sample being flowed through the flow cell. Rare cellular events are generally defined as events comprising less than 5% of a total number of cells in the sample. Alternatively, the rare cellular events may be defined by events comprising less than 2% of a total number of cells in the sample; less than 1% of a total number of cells in the sample; and/or less than 0.1% of a total number of cells in the sample. The rare cellular events may be selected from the group consisting of: circulating tumor cells; fetal cells in maternal blood; cancer cells; liver cells; kidney cells; and circulating stem cells.

The analyzer may further comprise: (7) optical lenses disposed between the laser and the flow cell; and/or (8) a sorter coupled to the processor. The optical lenses may be configured to affect a spot size and/or spot shape of the laser beam. The spot size may be greater than 20 µm in one direction; greater than 40 µm in one direction; and/or the spot shape may be elliptical with the spot size having a width greater than 20 µm, and a length greater than 40 µm. The sorter may be configured to separate the rare cellular events from the sample, based on detection by the processor.

The deflector component may be configured to sweep the laser beam across an area of the flow cell. For example, the deflector component may be configured to sweep the laser beam back-and-forth in a direction perpendicular to the sample flow, at a horizontal scan speed of greater than 200 m/s or greater than 300 m/s. The deflector component may also be configured to sweep the laser beam up-and-down in a direction parallel to the sample flow, at a vertical scan speed of greater than 10 m/s or greater than 15 m/s. The flow rate through the flow cell may be greater than one million cells per second; greater than two million cells per second; greater than three million cells per second; greater than 120 µL/s; and/or greater than 240 µL/s.

The cell-binding surface markers may be cancer cell binding surface markers; and/or fluorophore-conjugated monoclonal antibodies. The sample may be subjected to a lysis-free single dilution comprising the cell-binding surface markers, or a lysis reagent comprising the cell-binding surface markers.

The processor may include one or more field-programmable gate arrays configured to operate at 100 MHz or more; and/or at 300 MHz or more. In another embodiment, the processor may be a relatively "low grade" processor, having one or more field-programmable gate arrays configured to operate at under 300 MHz; and/or under 100 MHz.

A cross-section of the core stream of the sample flow may be configured to be greater than 100 µm in one dimension; greater than 200 µm in one dimension; and/or an elliptical shape with a depth greater than 100 µm and a width greater than 200 µm.

In another embodiment, there is provided a system for the detection of rare cellular events, wherein rare cellular events are defined by events comprising less than 5% of a total number of cells in the sample. The system comprises: (1) means for flowing a sample through a flow cell at a flow rate greater than 300,000 cells per second; (2) means for subjecting the sample to a scanning focused light source (e.g., laser beam, focused LED light source, or equivalent light source) directed to the flow cell; (3) means for detecting fluorescence emission from the sample; (4) means for detecting light scatter emitted from the sample; and/or (5) means for distinguishing rare cellular events in the sample based on fluorescence emission from cell-binding surface markers introduced into the sample prior to the sample being flowed through the flow cell. The system may further comprise: (6) means for affecting a spot size of the focused light beam; and/or (7) means for sorting the rare cellular events from the sample.

The scanning of the focused light beam may be performed at a horizontal scan speed of greater than 200 m/s (or greater than 300 m/s), and a vertical scan speed of greater than 10 m/s (or greater than 15 m/s). The spot size may be greater than 20 µm in one direction; greater than 40 µm in one direction; and/or the spot shape may be elliptical with the spot size having a width greater than 20 µm, and a length greater than 40 µm. The flow rate of the sample through the flow cell may be greater than one million cells per second; greater than two million cells per second; greater than three million cells per second; greater than 120 µL/s; and/or greater than 240 µL/s.

The cell-binding surface markers may be cancer cell binding surface markers; and/or fluorophore-conjugated monoclonal antibodies. The sample may be subjected to a lysis-free single dilution comprising the cell-binding surface markers, or a lysis reagent comprising the cell-binding surface markers. The rare cellular events may be defined by events comprising less than 2% of a total number of cells in the sample; less than 1% of a total number of cells in the sample; and/or less than 0.1% of a total number of cells in the sample. The rare cellular events may be selected from the group consisting of: circulating tumor cells; fetal cells in maternal blood; cancer cells; liver cells; kidney cells; and circulating stem cells.

A cross-section of a core stream of the sample flow may be configured to be greater than 100 µm in one dimension; greater than 200 µm in one dimension; and/or an elliptical shape with a depth greater than 100 µm and a width greater than 200 µm.

In still another embodiment, there is provided a flow cytometry method for the detection of rare cellular events, wherein rare cellular events are defined by events comprising less than 5% of a total number of cells in the sample. The method comprises: (1) flowing a sample through a flow cell dimensioned so as to permit a flow rate greater than 300,000 cells per second; (2) scanning a laser beam (or equivalent focused light beam) across an area of the sample in the flow cell; (3) detecting fluorescence emission from cell-binding surface markers introduced into the sample prior to the sample being flowed through the flow cell; and (4) identifying rare cellular events based on the fluorescence emission. The method may further comprise: sorting the rare cellular events based on the identification step.

The scanning of the laser beam may be performed at a horizontal scan speed of greater than 200 m/s (or greater than 300 m/s), and a vertical scan speed of greater than 10 m/s (or greater than 15 m/s). The spot size may be greater than 20 µm in one direction; greater than 40 µm in one direction; and/or the spot shape may be elliptical with the spot size having a width greater than 20 µm, and a length greater than 40 µm. The flow rate of the sample through the flow cell may be greater than one million cells per second; greater than two million cells per second; greater than three million cells per second; greater than 120 µL/s; and/or greater than 240 µL/s.

The cell-binding surface markers may be cancer cell binding surface markers; and/or fluorophore-conjugated monoclonal antibodies. The sample may be subjected to a lysis-free single dilution comprising the cell-binding surface markers, or a lysis reagent comprising the cell-binding surface markers. The rare cellular events may be defined by events comprising less than 2% of a total number of cells in the sample; less than 1% of a total number of cells in the sample; and/or less than 0.1% of a total number of cells in the sample. The rare cellular events may be selected from the group consisting of: circulating tumor cells; fetal cells in maternal blood; cancer cells; liver cells; kidney cells; and circulating stem cells.

A cross-section of a core stream of the sample flow may be configured to be greater than 100 µm in one dimension; greater than 200 µm in one dimension; and/or an elliptical shape with a depth greater than 100 µm and a width greater than 200 µm.

Since typically a number of distinct antibodies are necessary to discriminate cells of interest from background, interfering, or simply similar but nontarget cells, a corresponding number of optical collection channels, designed to accept fluorescent light from the respective conjugated fluorophores, may be implemented. The optical design may be such that light collection is maximized due to the often low level of emitted light in surface-antigen assays or other fluorescent assays. The optical collection channels should be spectrally optimized to allow for the least cross-talk between channels and for the greatest collection of in-band emitted light.

In another embodiment, the design of the optical interaction mechanism is modified. Since the absolute magnitude of the signal is not of particular importance, while the throughput is of utmost importance, the design aims to maximize throughput of analyte material through the flow cell. The design may sacrifice the linearity or uniformity of the signal across the scan range. Accordingly, the flow cell dimensions, the sheath-fluid injection rate, the core stream injection rate, the rastering beam dimensions, the raster scan range, and the rastering frequency are designed so as to maximize the volume per unit time of core stream positively interrogated by the laser beam. One way to do so is to make the laser beam larger than a typical LRFC beam, boost the laser power significantly in order to both compensate for the larger beam spot size and for the increased sensitivity requirements, and to make the core stream deeper.

Sorting modules can be adapted to the optical module described above to trigger on select optical channel signals and divert the corresponding cells of interest onto a separate stream for segregated collection.

In one embodiment, the invention is directed toward one or more computer systems capable of carrying out the functionality described herein. For example, any of the method/analysis steps discussed herein may be implemented in a computer system having one or more processors, a data communication infrastructure (e.g., a communications bus, cross-over bar, or network), a display interface, and/or a storage or memory unit. The storage or memory unit may include computer-readable storage medium with instructions (e.g., control logic or software) that, when executed, cause the processor(s) to perform one or more of the functions described herein. The terms "computer-readable storage medium," "computer program medium," and "computer usable medium" are used to generally refer to media such as a removable storage drive, removable storage units, data transmitted via a communications interface, and/or a hard disk installed in a hard disk drive. Such computer program products provide computer software, instructions, and/or data to a computer system, which also serve to transform the computer system from a general purpose computer into a special purpose computer programmed to perform the particular functions described herein. Where appropriate, the processor, associated components, and equivalent systems and sub-systems thus serve as examples of "means for" performing select operations and functions. Such "means for" performing select operations and functions also serve to transform a general purpose computer into a special purpose computer programmed to perform said select operations and functions.

Conclusion

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. A flow cytometry analyzer for the detection of rare cellular events in a sample containing a plurality of cells, the analyzer comprising:
   a flow cell dimensioned so as to permit a flow of a sample through the flow cell at a flow rate greater than 300,000 cells per second;
   a laser positioned to emit a laser beam directed to the flow cell;
   a deflector component disposed between the laser and the flow cell, wherein the deflector component is configured to affect a position of the laser beam relative to the sample flow;
   a fluorescence emission detector;
   a processor, and
   a memory unit comprising a computer-readable storage medium programmed with instructions that, when executed, cause the processor to:
   contact the sample with one or more cell binding surface markers used to identify one or more rare cellular events;
   pass the sample through the flow cell at a flow rate greater than 300,000 cells per second.
   direct the laser beam toward the flow cell;
   sweep the laser beam across an area of interrogation within the flow cell using the deflector component;
   detect a plurality of light scatter and/or fluorescence emission signals from the cells in the sample; and
   analyze the detected light scatter and/or fluorescence emission signals to identify one or more rare cellular events within the sample.

2. The analyzer of claim 1, wherein the computer-readable storage medium comprises instructions to sweep the laser beam back-and-forth in a direction that is perpendicular to a sample flow direction.

3. The analyzer of claim 2, wherein the computer-readable storage medium comprises instructions to sweep the laser beam at a horizontal scan speed of greater than 200 m/s.

4. The analyzer of claim 2, wherein the computer-readable storage medium comprises instructions to sweep the laser beam at a horizontal scan speed of greater than 300 m/s.

5. The analyzer of claim 1, wherein the computer-readable storage medium comprises instructions to sweep the laser beam up-and-down in a direction parallel to the sample flow.

6. The analyzer of claim 5, wherein the computer-readable storage medium comprises instructions to sweep the laser beam at a vertical scan speed of greater than 10 m/s.

7. The analyzer of claim 5, wherein the computer-readable storage medium comprises instructions to sweep the laser beam at a vertical scan speed of greater than 15 m/s.

8. The analyzer of claim 1, further comprising:
   an optical lens disposed between the laser and the flow cell, wherein the optical lens is configured to affect a spot size of the laser beam, wherein the spot size is greater than 20 µm in one direction.

9. The analyzer of claim 1, further comprising:
an optical lens disposed between the laser and the flow cell, wherein the optical lens is configured to affect a spot size of the laser beam, wherein the spot size is greater than 40 μm in one direction.

10. The analyzer of claim 1, further comprising:
an optical lens disposed between the laser and the flow cell, wherein the optical lens is configured to affect a spot size and a spot shape of the laser beam, wherein the spot shape is elliptical and the spot size has a width greater than 20 μm, and a length greater than 40 μm.

11. The analyzer of claim 1, wherein the computer-readable storage medium comprises instructions to move the sample through the flow cell at a flow rate that is greater than one million cells per second.

12. The analyzer of claim 1, wherein the computer-readable storage medium comprises instructions to move the sample through the flow cell at a flow rate that is greater than two million cells per second.

13. The analyzer of claim 1, wherein the computer-readable storage medium comprises instructions to move the sample through the flow cell at a flow rate that is greater than 120 μL/s.

14. The analyzer of claim 1, wherein a the computer-readable storage medium comprises instructions to move the sample through the flow cell at a flow rate that is greater than 240 μL/s.

15. The analyzer of claim 1, wherein the computer-readable storage medium comprises instructions to subject the sample to a lysis-free single dilution comprising the cell-binding surface markers.

16. The analyzer of claim 1, wherein the computer-readable storage medium comprises instructions to subject the sample to a lysis reagent comprising the cell-binding surface markers.

17. The analyzer of claim 1, wherein the processor includes a field-programmable gate array configured to operate at 100 MHz or more.

18. The analyzer of claim 1, wherein the processor includes a field-programmable gate array configured to operate at 300 MHz or more.

19. The analyzer of claim 1, wherein the computer-readable storage medium comprises instructions to move the sample through the flow cell in a manner such that a cross-section of a core stream of the sample as it passes through the flow cell is greater than 100 μm in one dimension.

20. The analyzer of claim 1, wherein the computer-readable storage medium comprises instructions to move the sample through the flow cell in a manner such that a cross-section of a core stream of the sample as it passes through the flow cell is greater than 200 μm in one dimension.

21. The analyzer of claim 1, wherein the computer-readable storage medium comprises instructions to move the sample through the flow cell in a manner such that a cross-section of a core stream of the sample as it passes through the flow cell is an elliptical shape with a depth greater than 100 μm and a width greater than 200 μm.

22. The analyzer of claim 1, further comprising:
a sorter coupled to the processor, wherein the computer-readable storage medium comprises instructions to separate the rare cellular events from the sample, using the sorter, based on the analysis of the light scatter and/or fluorescence emission signals by the processor.

* * * * *